United States Patent
Cao

(10) Patent No.: US 6,262,228 B1
(45) Date of Patent: Jul. 17, 2001

(54) IRAK3 POLYPEPTIDES AND METHODS

(75) Inventor: Zhaodan Cao, South San Francisco, CA (US)

(73) Assignee: Tularik Inc., South San Francisco, CA (US)

( * ) Notice: Subject to any disclaimer, the term of this patent is extended or adjusted under 35 U.S.C. 154(b) by 0 days.

(21) Appl. No.: 09/135,232

(22) Filed: Aug. 17, 1998

(51) Int. Cl.$^7$ .......................... A61K 38/00; C07K 14/00; C07K 16/00; C07K 17/00; G01N 33/53
(52) U.S. Cl. ..................... 530/300; 435/7.1; 435/7.2; 530/324; 530/326; 530/327; 530/328; 530/329; 530/350; 530/351
(58) Field of Search .................................... 530/351, 350, 530/300, 324, 326, 327, 328, 329; 514/2, 8, 12; 435/7.1, 7.2

(56) References Cited

FOREIGN PATENT DOCUMENTS

| 8103277 | * | 4/1996 | (JP) . |
| 9700690 | * | 1/1997 | (WO) . |
| 9743427 | * | 11/1997 | (WO) . |

OTHER PUBLICATIONS

Burns, K., et al. (1998) *J. Biol. Chem* 273: 12203–09, May, 1998.*
Wesche, H., et al. (1999) *J. Biol. Chem.* 274: 19403–10.*
Martin et al, *Science,* 262, 1993, p 1432 (abst.).*
Maran et al, *Biochem. Biophys. Acta* 1216, 1993, p 9–14 (abst only).*

* cited by examiner

*Primary Examiner*—Gary L. Kunz
*Assistant Examiner*—Robert S. Landsman
(74) *Attorney, Agent, or Firm*—Richard Aron Osman

(57) ABSTRACT

The invention provides methods and compositions relating to a novel kinase, IRAK3. The polypeptides may be produced recombinantly from transformed host cells from the disclosed IRAK3 encoding nucleic acids or purified from human cells. The invention provides isolated IRAK3 hybridization probes and primers capable of specifically hybridizing with the disclosed IRAK3 genes, IRAK3-specific binding agents such as specific antibodies, and methods of making and using the subject compositions in diagnosis, therapy and in the biopharmaceutical industry.

38 Claims, No Drawings

SEQUENCE LISTING

<160> NUMBER OF SEQ ID NOS: 2

<210> SEQ ID NO 1
<211> LENGTH: 2288
<212> TYPE: DNA
<213> ORGANISM: human
<220> FEATURE:
<221> NAME/KEY: CDS
<222> LOCATION: (64)..(1851)

<400> SEQUENCE: 1
gcctgtcgca ggcgtgcagg gacctggact ccgcctcgtc cccggggctc gggcagccga      60 gcc atg gcg ggg aac tgt ggg gcc cgc ggc gcg ctg tcg gcg cac acg     108

```
          Met Ala Gly Asn Cys Gly Ala Arg Gly Ala Leu Ser Ala His Thr
            1               5                  10                 15 ctg ctg ttc gac ctg ccg ccc gcg ctg ctc gga gag ctc tgc gct gtt          156
Leu Leu Phe Asp Leu Pro Pro Ala Leu Leu Gly Glu Leu Cys Ala Val
                20                  25                  30 ctg gac agc tgc gac ggc gcg ctg ggc tgg cgc ggc ctg gca gag aga          204
Leu Asp Ser Cys Asp Gly Ala Leu Gly Trp Arg Gly Leu Ala Glu Arg
            35                  40                  45 ctt tca agc agc tgg ctg gat gtt cgt cat att gaa aag tat gta gac          252
Leu Ser Ser Ser Trp Leu Asp Val Arg His Ile Glu Lys Tyr Val Asp
        50                  55                  60 caa ggt aaa agt gga aca aga gaa tta ctt tgg tcc tgg gca cag aaa          300
Gln Gly Lys Ser Gly Thr Arg Glu Leu Leu Trp Ser Trp Ala Gln Lys
    65                  70                  75 aac aag acc atc ggt gac ctt tta cag gtc ctc cag gag atg gga cat          348
Asn Lys Thr Ile Gly Asp Leu Leu Gln Val Leu Gln Glu Met Gly His
 80                  85                  90                  95 cgt cga gct att cat tta att aca aac tat gga gca gtg ttg agt cct          396
Arg Arg Ala Ile His Leu Ile Thr Asn Tyr Gly Ala Val Leu Ser Pro
                100                 105                 110 tca gag aag agt tat cag gaa ggt gga ttt cca aat ata tta ttc aag          444
Ser Glu Lys Ser Tyr Gln Glu Gly Gly Phe Pro Asn Ile Leu Phe Lys
            115                 120                 125 gaa aca gcc aat gtc acc gtg gat aat gtt ctt att cct gaa cat aat          492
Glu Thr Ala Asn Val Thr Val Asp Asn Val Leu Ile Pro Glu His Asn
        130                 135                 140 gaa aaa gga gta ctg ctt aaa tct tcc atc agc ttt caa aat atc ata          540
Glu Lys Gly Val Leu Leu Lys Ser Ser Ile Ser Phe Gln Asn Ile Ile
    145                 150                 155 gaa gga act aga aat ttc cac aaa gac ttc cta att gga gaa gga gag          588
Glu Gly Thr Arg Asn Phe His Lys Asp Phe Leu Ile Gly Glu Gly Glu
160                 165                 170                 175 att ttt gag gta tac aga gtg gag att caa aac cta aca tat gct gtc          636
Ile Phe Glu Val Tyr Arg Val Glu Ile Gln Asn Leu Thr Tyr Ala Val
                180                 185                 190 aaa tta ttt aaa cag gag aaa aaa atg cag tgt aag aag cat tgg aag          684
Lys Leu Phe Lys Gln Glu Lys Lys Met Gln Cys Lys Lys His Trp Lys
            195                 200                 205 agg ttt tta tct gag ctt gaa gtt tta cta ctg ttt cat cac cca aac          732
Arg Phe Leu Ser Glu Leu Glu Val Leu Leu Leu Phe His His Pro Asn
        210                 215                 220 ata cta gag ttg gct gca tat ttt aca gag act gag aag ttc tgt ctg          780
Ile Leu Glu Leu Ala Ala Tyr Phe Thr Glu Thr Glu Lys Phe Cys Leu
    225                 230                 235 att tat cca tac atg aga aat gga aca ctt ttt gac aga ttg cag tgt          828
Ile Tyr Pro Tyr Met Arg Asn Gly Thr Leu Phe Asp Arg Leu Gln Cys
240                 245                 250                 255 gta ggt gac acg gcc cca ctc cct tgg cac att cga atc ggt ata tta          876
Val Gly Asp Thr Ala Pro Leu Pro Trp His Ile Arg Ile Gly Ile Leu
                260                 265                 270 ata gga ata tcc aaa gcc att cac tac ctg cac aac gtt caa cca tgc          924
Ile Gly Ile Ser Lys Ala Ile His Tyr Leu His Asn Val Gln Pro Cys
            275                 280                 285 tcg gtc atc tgt ggc agt ata tca agt gca aac atc ctt ttg gat gat          972
Ser Val Ile Cys Gly Ser Ile Ser Ser Ala Asn Ile Leu Leu Asp Asp
        290                 295                 300 cag ttt caa ccc aaa cta act gat ttt gcc atg gca cac ttc cgg tcc         1020
Gln Phe Gln Pro Lys Leu Thr Asp Phe Ala Met Ala His Phe Arg Ser
    305                 310                 315
```

-continued

| | | |
|---|---|---|
| cac cta gaa cat cag agt tgt acc ata aat atg acc agc agc agc agt<br>His Leu Glu His Gln Ser Cys Thr Ile Asn Met Thr Ser Ser Ser Ser<br>320                          325                   330                       335 | 1068 |

```
cac cta gaa cat cag agt tgt acc ata aat atg acc agc agc agc agt      1068
His Leu Glu His Gln Ser Cys Thr Ile Asn Met Thr Ser Ser Ser Ser
320                 325                 330                 335 aaa cat ctg tgg tac atg cca gaa gag tac atc aga cag ggg aaa ctt      1116
Lys His Leu Trp Tyr Met Pro Glu Glu Tyr Ile Arg Gln Gly Lys Leu
                    340                 345                 350 tcc att aaa aca gat gtc tac agc ttt gga att gta ata atg gaa gtt      1164
Ser Ile Lys Thr Asp Val Tyr Ser Phe Gly Ile Val Ile Met Glu Val
                355                 360                 365 cta aca gga tgt aga gta gtg tta gat gat cca aaa cat atc cag ctg      1212
Leu Thr Gly Cys Arg Val Val Leu Asp Asp Pro Lys His Ile Gln Leu
            370                 375                 380 cgg gat ctc ctt aga gaa ttg atg gag aag aga ggc ctg gat tca tgt      1260
Arg Asp Leu Leu Arg Glu Leu Met Glu Lys Arg Gly Leu Asp Ser Cys
385                 390                 395 ctc tca ttt cta gat aag aaa gtg cct ccc tgc cct cgg aat ttc tct      1308
Leu Ser Phe Leu Asp Lys Lys Val Pro Pro Cys Pro Arg Asn Phe Ser
400                 405                 410                 415 gcc aag ctc ttc tgt ttg gca ggc cgg tgt gct gca acg cgg gca aag      1356
Ala Lys Leu Phe Cys Leu Ala Gly Arg Cys Ala Ala Thr Arg Ala Lys
                    420                 425                 430 tta aga cca tca atg gat gaa gtt tta aat act ctt gaa agt act caa      1404
Leu Arg Pro Ser Met Asp Glu Val Leu Asn Thr Leu Glu Ser Thr Gln
                435                 440                 445 gcc agc ttg tat ttt gct gaa gat cct ccc aca tca cta aag tcc ttc      1452
Ala Ser Leu Tyr Phe Ala Glu Asp Pro Pro Thr Ser Leu Lys Ser Phe
            450                 455                 460 agg tgt cct tct cct cta ttc ctg gag aat gta cca agt att cca gtg      1500
Arg Cys Pro Ser Pro Leu Phe Leu Glu Asn Val Pro Ser Ile Pro Val
465                 470                 475 gaa gat gat gaa agc cag aat aac aat tta cta cct tct gat gaa ggc      1548
Glu Asp Asp Glu Ser Gln Asn Asn Asn Leu Leu Pro Ser Asp Glu Gly
480                 485                 490                 495 ctg agg ata gac aga atg act cag aaa act cct ttt gaa tgc agc cag      1596
Leu Arg Ile Asp Arg Met Thr Gln Lys Thr Pro Phe Glu Cys Ser Gln
                    500                 505                 510 tct gag gtt atg ttt ctg agc ttg gac aaa aag cca gag agc aag aga      1644
Ser Glu Val Met Phe Leu Ser Leu Asp Lys Lys Pro Glu Ser Lys Arg
                515                 520                 525 aat gag gaa gct tgc aac atg ccc agt tct tct tgt gaa gaa agt tgg      1692
Asn Glu Glu Ala Cys Asn Met Pro Ser Ser Ser Cys Glu Glu Ser Trp
            530                 535                 540 ttc cca aag tat ata gtt cca tcc cag gac tta agg ccc tat aag gta      1740
Phe Pro Lys Tyr Ile Val Pro Ser Gln Asp Leu Arg Pro Tyr Lys Val
545                 550                 555 aat ata gat cct tct tca gaa gct cca ggg cat tct tgc agg agc agg      1788
Asn Ile Asp Pro Ser Ser Glu Ala Pro Gly His Ser Cys Arg Ser Arg
560                 565                 570                 575 cca gtg gag agc agc tgt tcc tcc aaa ttt tcc tgg gat gaa tat gaa      1836
Pro Val Glu Ser Ser Cys Ser Ser Lys Phe Ser Trp Asp Glu Tyr Glu
                    580                 585                 590 cag tac aaa aaa gaa taaattctac cagaagataa agaaaaaagc aagtattgca      1891
Gln Tyr Lys Lys Glu
            595 taggcacctg agcataggta tgaccttggg aagacattgg ctccataagc aatgccaaga   1951 gaatgatcaa tagtgagttt gggtgatgca gataaacaat ctggataatt ccatttcttt   2011 tttcccaaac cctcaaacag agtgccttaa aaaattgttt tatcaggata attgtctcat   2071 gaccaaatcc acgctcaatt agagccattc aaaattcctt aagatcatgg gttctgactt   2131
```

```
cagccaaaca aaacaatcaa aacctaccaa aaagggactg gattgtaatg tcctctccat   2191
catcctcagt gtgagtcctc agagcctcca tctgccaaga acattcagtt ggattccatc   2251
gtttggttta gcttgcttgc acgggttgta ggaaatg                            2288
```

<210> SEQ ID NO 2
<211> LENGTH: 596
<212> TYPE: PRT
<213> ORGANISM: human

<400> SEQUENCE: 2

```
Met Ala Gly Asn Cys Gly Ala Arg Gly Ala Leu Ser Ala His Thr Leu
 1               5                  10                  15

Leu Phe Asp Leu Pro Pro Ala Leu Leu Gly Glu Leu Cys Ala Val Leu
            20                  25                  30

Asp Ser Cys Asp Gly Ala Leu Gly Trp Arg Gly Leu Ala Glu Arg Leu
        35                  40                  45

Ser Ser Ser Trp Leu Asp Val Arg His Ile Glu Lys Tyr Val Asp Gln
    50                  55                  60

Gly Lys Ser Gly Thr Arg Glu Leu Leu Trp Ser Trp Ala Gln Lys Asn
65                  70                  75                  80

Lys Thr Ile Gly Asp Leu Leu Gln Val Leu Gln Glu Met Gly His Arg
                85                  90                  95

Arg Ala Ile His Leu Ile Thr Asn Tyr Gly Ala Val Leu Ser Pro Ser
            100                 105                 110

Glu Lys Ser Tyr Gln Glu Gly Gly Phe Pro Asn Ile Leu Phe Lys Glu
        115                 120                 125

Thr Ala Asn Val Thr Val Asp Asn Val Leu Ile Pro Glu His Asn Glu
    130                 135                 140

Lys Gly Val Leu Leu Lys Ser Ser Ile Ser Phe Gln Asn Ile Ile Glu
145                 150                 155                 160

Gly Thr Arg Asn Phe His Lys Asp Phe Leu Ile Gly Glu Gly Glu Ile
                165                 170                 175

Phe Glu Val Tyr Arg Val Glu Ile Gln Asn Leu Thr Tyr Ala Val Lys
            180                 185                 190

Leu Phe Lys Gln Glu Lys Lys Met Gln Cys Lys Lys His Trp Lys Arg
        195                 200                 205

Phe Leu Ser Glu Leu Glu Val Leu Leu Leu Phe His His Pro Asn Ile
    210                 215                 220

Leu Glu Leu Ala Ala Tyr Phe Thr Glu Thr Glu Lys Phe Cys Leu Ile
225                 230                 235                 240

Tyr Pro Tyr Met Arg Asn Gly Thr Leu Phe Asp Arg Leu Gln Cys Val
                245                 250                 255

Gly Asp Thr Ala Pro Leu Pro Trp His Ile Arg Ile Gly Ile Leu Ile
            260                 265                 270

Gly Ile Ser Lys Ala Ile His Tyr Leu His Asn Val Gln Pro Cys Ser
        275                 280                 285

Val Ile Cys Gly Ser Ile Ser Ser Ala Asn Ile Leu Leu Asp Asp Gln
    290                 295                 300

Phe Gln Pro Lys Leu Thr Asp Phe Ala Met Ala His Phe Arg Ser His
305                 310                 315                 320

Leu Glu His Gln Ser Cys Thr Ile Asn Met Thr Ser Ser Ser Ser Lys
                325                 330                 335

His Leu Trp Tyr Met Pro Glu Glu Tyr Ile Arg Gln Gly Lys Leu Ser
```

-continued

```
                    340                 345                 350
Ile Lys Thr Asp Val Tyr Ser Phe Gly Ile Val Ile Met Glu Val Leu
        355                 360                 365

Thr Gly Cys Arg Val Val Leu Asp Asp Pro Lys His Ile Gln Leu Arg
        370                 375                 380

Asp Leu Leu Arg Glu Leu Met Glu Lys Arg Gly Leu Asp Ser Cys Leu
385                 390                 395                 400

Ser Phe Leu Asp Lys Lys Val Pro Pro Cys Pro Arg Asn Phe Ser Ala
            405                 410                 415

Lys Leu Phe Cys Leu Ala Gly Arg Cys Ala Ala Thr Arg Ala Lys Leu
            420                 425                 430

Arg Pro Ser Met Asp Glu Val Leu Asn Thr Leu Glu Ser Thr Gln Ala
        435                 440                 445

Ser Leu Tyr Phe Ala Glu Asp Pro Pro Thr Ser Leu Lys Ser Phe Arg
    450                 455                 460

Cys Pro Ser Pro Leu Phe Leu Glu Asn Val Pro Ser Ile Pro Val Glu
465                 470                 475                 480

Asp Asp Glu Ser Gln Asn Asn Asn Leu Leu Pro Ser Asp Glu Gly Leu
            485                 490                 495

Arg Ile Asp Arg Met Thr Gln Lys Thr Pro Phe Glu Cys Ser Gln Ser
            500                 505                 510

Glu Val Met Phe Leu Ser Leu Asp Lys Lys Pro Glu Ser Lys Arg Asn
        515                 520                 525

Glu Glu Ala Cys Asn Met Pro Ser Ser Ser Cys Glu Glu Ser Trp Phe
        530                 535                 540

Pro Lys Tyr Ile Val Pro Ser Gln Asp Leu Arg Pro Tyr Lys Val Asn
545                 550                 555                 560

Ile Asp Pro Ser Ser Glu Ala Pro Gly His Ser Cys Arg Ser Arg Pro
            565                 570                 575

Val Glu Ser Ser Cys Ser Ser Lys Phe Ser Trp Asp Glu Tyr Glu Gln
            580                 585                 590

Tyr Lys Lys Glu
        595
```

IRAK3 POLYPEPTIDES AND METHODS

FIELD OF THE INVENTION

The field of this invention is enzymes involved in signal transduction.

BACKGROUND

Interleukin 1 (IL-1) receptor associated kinase (IRAK) functions as an intracellular signal transducer for the pro-inflammatory cytokine IL-1. IL-1 treatment of cells induces the complex formation of the two IL-1 receptor chains, IL-1R1 and IL-1RAcP, which recruits an adaptor molecule designated as MyD88 which binds to IRAK. IRAK is subsequently phosphorylated, released from the receptor complex to interact with TRAF6. TRAF6 triggers either the NIK/IKK kinase cascade to activate the transcription factor NF-κB or an undefined kinase cascade to activate the transcription factor AP-1. Both transcription factors regulate large numbers of genes that regulate immune and inflammatory responses.

The genome project has facilitated the identification of a large number of membrane bound receptor-like molecules that are related to IL-1RI and IL-1RAcP by sequence homology. One member of this family, IL-1RrP, has been recently shown to function as a receptor of an IL-1 related cytokine, IL-1 8, that regulates immune response by promoting the production of interferony. Like IL-1RI and IL-1RAcP, IL-1RrP signals NF-κB activation. Gene disruption experiments and biochemical analyzes indicate that IL-1RrP also utilizes MyD88 and IRAK and TRAF6 as intracellular signal transducers.

Although MyD88 deficient mice failed to respond to IL-1 and IL-18, IRAK deficient mice still have a residual response to IL-1. This observation indicates that other molecules in the cells can partially substitute for the function of IRAK in IL-1 signaling. Recently, an IRAK-related molecule designated IRAK2, was described. Although upon over expression, IRAK2 could interact with IL-1R and IRAK, it has not been shown to be recruited to the receptor complex after IL-1 treatment like IRAK. Therefore, we searched for molecules that can substitute for IRAK in an IL-1 response.

SUMMARY OF THE INVENTION

The invention provides methods and compositions relating to isolated IRAK3 polypeptides and related polynucleotides having IRAK3-specific structure and activity. The subject IRAK3 polypeptides and polynucleotides can regulate cellular responsiveness to cytokine activation and hence provide important regulators of cell function. The polypeptides may be produced recombinantly from transformed host cells from the subject IRAK3 polypeptide encoding nucleic acids or purified from mammalian cells. The invention provides isolated IRAK3 hybridization probes and primers capable of specifically hybridizing with the disclosed IRAK3 gene, IRAK3-specific binding agents such as specific antibodies, and methods of making and using the subject compositions in diagnosis (e.g. genetic hybridization screens for IRAK3 transcripts), therapy (e.g. IRAK3 kinase inhibitors to inhibit IL-1 induced signal transduction) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

The nucleotide sequence of a natural human cDNA encoding a human IRAK3 polypeptide is shown as SEQ ID NO:1, and the full conceptual translate is shown as SEQ ID NO:2. To clone this novel IRAK3 cDNA, we used a the cDNA insert from a mouse EST clone (AA840598, Genome Systems) as a hybridization probe to screen a lambda cDNA library constructed with Phytohemagglutinin-L (PHA-L) activated human peripheral blood leukocytes under low stringent conditions. We isolated a 2.2 kb cDNA clone with an open reading frame encoding 617 amino acids, and determined that the methionine at position 22 of the open reading frame is the first amino acid of the full-length IRAK3 protein, which consists of 596 amino acids with a calculated molecular weight of 67675 daltons. We determined that IRAK3 can function as a signaling molecule for either IL-1 or cytokines that signal through IL-1R related receptors, can bind MyD88 in coexpression and in vitro binding assays, and plays a role in inflammatory responses and/or immune regulation and thus provides a drug target for treatment of inflammatory diseases and immune disorders.

The IRAK3 polypeptides of the invention include incomplete translates of SEQ ID NO:1 which translates and fragments of SEQ ID NO:2 have human IRAK3-specific amino acid sequence, binding specificity or function. Preferred translates/deletion mutants comprise at least 10, preferably at least 15, more preferably at least 25, more preferably at least 35, most preferably at least 50 consecutive residues of SEQ ID NO:2, preferably of at least one of SEQ ID NO:2, residues 1–99, residues 100–199, residues 200–299, residues 300–399, residues 400–499 and residues 500–596. The subject domains provide IRAK3 domain specific activity or function, such as IRAK3-specific kinase or kinase inhibitory activity, IRAK-3 specific MyD88-binding or binding inhibitory activity, IRAK3 specific antibody binding or binding inhibitory activity.

IRAK3-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an IRAK3 polypeptide with a binding target is evaluated. The binding target may be a natural intracellular binding target such as an IRAK3 substrate, an IRAK3 regulating protein or other regulator that directly modulates IRAK3 activity or its localization such as MyD88; or non-natural binding target such a specific immune protein such as an antibody, or an IRAK3 specific agent such as those identified in screening assays such as described below. IRAK3-binding specificity may be assayed by kinase activity or binding equilibrium constants (usually at least about $10^7 M^{-1}$, preferably at least about $10^8 M^{-1}$, more preferably at least about $10^9 M^{-1}$), by the ability of the subject polypeptide to function as negative mutants in IRAK3-expressing cells, to elicit IRAK3 specific antibody in a heterologous host (e.g a rodent or rabbit), etc. In any event, the IRAK3 binding specificity of the subject IRAK3 polypeptides distinguishes any discernable translation product of EST clone AA840598.

In a particular embodiment, the subject domains provide IRAK3-specific antigens and/or immunogens, especially when coupled to carrier proteins. For example, peptides corresponding to IRAK3-specific domains are covalently coupled to keyhole limpet antigen (KLH) and the conjugate is emulsified in Freunds complete adjuvant. Laboratory rabbits are immunized according to conventional protocol and bled. The presence of IRAK3-specific antibodies is assayed by solid phase immunosorbant assays using immobilized IRAK3 polypeptides of SEQ ID NO:2, see, e.g. Table 2.

TABLE 2

Immunogenic IRAK3 polypeptides eliciting IRAK3-specific rabbit polyclonal antibody: IRAK3 polypeptide-KLH conjugates immunized per protocol described above.

| IRAK3 Polypeptide Sequence | Immunogenicity |
| --- | --- |
| SEQ ID NO:2, residues 1–10 | +++ |
| SEQ ID NO:2, residues 12–21 | +++ |
| SEQ ID NO:2, residues 25–37 | +++ |
| SEQ ID NO:2, residues 42–59 | +++ |
| SEQ ID NO:2, residues 62–71 | +++ |
| SEQ ID NO:2, residues 72–85 | +++ |
| SEQ ID NO:2, residues 88–89 | +++ |
| SEQ ID NO:2, residues 105–112 | +++ |
| SEQ ID NO:2, residues 116–122 | +++ |
| SEQ ID NO:2, residues 120–128 | +++ |
| SEQ ID NO:2, residues 175–182 | +++ |
| SEQ ID NO:2, residues 180–195 | +++ |
| SEQ ID NO:2, residues 201–208 | +++ |
| SEQ ID NO:2, residues 213–222 | +++ |
| SEQ ID NO:2, residues 222–230 | +++ |
| SEQ ID NO:2, residues 228–237 | +++ |
| SEQ ID NO:2, residues 230–338 | +++ |
| SEQ ID NO:2, residues 237–245 | +++ |
| SEQ ID NO:2, residues 440–450 | +++ |
| SEQ ID NO:2, residues 442–451 | +++ |
| SEQ ID NO:2, residues 445–452 | +++ |
| SEQ ID NO:2, residues 447–454 | +++ |
| SEQ ID NO:2, residues 449–456 | +++ |
| SEQ ID NO:2, residues 450–457 | +++ |
| SEQ ID NO:2, residues 471–480 | +++ |
| SEQ ID NO:2, residues 495–502 | +++ |
| SEQ ID NO:2, residues 501–510 | +++ |
| SEQ ID NO:2, residues 525–532 | +++ |
| SEQ ID NO:2, residues 527–540 | +++ |
| SEQ ID NO:2, residues 549–556 | +++ |
| SEQ ID NO:2, residues 563–575 | +++ |
| SEQ ID NO:2, residues 577–590 | +++ |
| SEQ ID NO:2, residues 589–596 | +++ |

The claimed IRAK3 polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The IRAK3 polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al, Greene Publ. Assoc., Wiley-Interscience, N.Y.) or that are otherwise known in the art.

The invention provides binding agents specific to the claimed IRAK3 polypeptides, including substrates, agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g. NF-κB activation. Novel IRAK3-specific binding agents include IRAK3-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate IRAK3 function, e.g. IRAK3-dependent transcriptional activation, esp. dominant negative deletion mutants, etc. Accordingly, the invention also provides methods for modulating signal transduction involving IL-1 receptor activation in a cell comprising the step of modulating IRAK3 kinase activity, e.g. by contacting the cell with a dominant negative IRAK3 deletion mutant, or IRAK3 polynucleotide (below).

The amino acid sequences of the disclosed IRAK3 polypeptides are used to back-translate IRAK3 polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural IRAK3-encoding nucleic acid sequences ("GCG" software, Genetics Computer Group, Inc, Madison Wis.). IRAK3-encoding nucleic acids used in IRAK3-expression vectors and incorporated into recombinant host cells, e.g. for expression and screening, transgenic animals, e.g. for functional studies such as the efficacy of candidate drugs for disease associated with IRAK3-modulated cell function, etc.

The invention also provides nucleic acid hybridization probes and replication/amplification primers having a IRAK3 cDNA specific sequence comprising SEQ ID NO:1 or fragments thereof, and sufficient to effect specific hybridization thereto (i.e. specifically hybridize with SEQ ID NO:1, particularly in the presence of EST clone AA840598. Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5× SSPE (0.18 M NaCl, 0.01 M NaPO$_4$, pH7.7, 0.001 M EDTA) buffer at a temperature of 42° C. and remaining bound when subject to washing at 42° C. with 0.2× SSPE; preferably hybridizing in a buffer comprising 50% formamide in 5× SSPE buffer at a temperature of 42° C. and remaining bound when subject to washing at 42° C. with 0.2× SSPE buffer at 42° C. IRAK3 nucleic acids can also be distinguished using alignment algorithms, such as BLASTX (Altschul et al. (1990) Basic Local Alignment Search Tool, J Mol Biol 215, 403–410).

TABLE 3

Exemplary IKAK3 nucleic acids which hybridize with a strand of SEQ ID NO:1 under Conditions I and/or II.

| IRAK3 Nucleic Acids | Specific Hybridization |
| --- | --- |
| SEQ ID NO:1, nucleotides 1–36 | + |
| SEQ ID NO:1, nucleotides 68–98 | + |
| SEQ ID NO:1, nucleotides 95–130 | + |
| SEQ ID NO:1, nucleotides 175–220 | + |
| SEQ ID NO:1, nucleotides 261–299 | + |
| SEQ ID NO:1, nucleotides 274–310 | + |
| SEQ ID NO:1, nucleotides 331–369 | + |
| SEQ ID NO:1, nucleotides 530–570 | + |
| SEQ ID NO:1, nucleotides 584–616 | + |
| SEQ ID NO:1, nucleotides 661–708 | + |
| SEQ ID NO:1, nucleotides 689–725 | + |
| SEQ ID NO:1, nucleotides 822–856 | + |
| SEQ ID NO:1, nucleotides 989–1012 | + |
| SEQ ID NO:1, nucleotides 1128–1165 | + |
| SEQ ID NO:1, nucleotides 1238–1258 | + |
| SEQ ID NO:1, nucleotides 1348–1372 | + |

TABLE 3-continued

Exemplary IKAK3 nucleic acids which hybridize with a strand of
SEQ ID NO:1 under Conditions I and/or II.

| IRAK3 Nucleic Acids | Specific Hybridization |
|---|---|
| SEQ ID NO:1, nucleotides 1465–1499 | + |
| SEQ ID NO:1, nucleotides 1562–1593 | + |
| SEQ ID NO:1, nucleotides 1657–1684 | + |
| SEQ ID NO:1, nucleotides 1705–1739 | + |
| SEQ ID NO:1, nucleotides 1822–1861 | + |
| SEQ ID NO:1, nucleotides 1917–1944 | + |
| SEQ ID NO:1, nucleotides 2035–2069 | + |
| SEQ ID NO:1, nucleotides 2161–2183 | + |
| SEQ ID NO:1, nucleotides 2250–2288 | + |

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NO:1, or fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of IRAK3 genes and gene transcripts and in detecting or amplifying nucleic acids encoding additional IRAK3 homologs and structural analogs. In diagnosis, IRAK3 hybridization probes find use in identifying wild-type and mutant IRAK3 alleles in clinical and laboratory samples. Mutant alleles are used to generate allele-specific oligonucleotide (ASO) probes for high-throughput clinical diagnoses. In therapy, therapeutic IRAK3 nucleic acids are used to modulate cellular expression or intracellular concentration or availability of active IRAK3.

The invention provides efficient methods of identifying agents, compounds or lead compounds for agents active at the level of a IRAK3 modulatable cellular function. Generally, these screening methods involve assaying for compounds which modulate IRAK3 interaction with a natural IRAK3 binding target such as MyD88. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an IRAK3 polypeptide, which may be part of a fusion product with another peptide or polypeptide, e.g. a tag for detection or anchoring, etc. The assay mixtures comprise a natural intracellular IRAK3 binding target. In a particular embodiment, the binding target is an MyD88-derived binding peptide or an IRAK3-derived substrate of IRAK3 kinase activity. While native full-length binding targets may be used, it is frequently preferred to use portions (e.g. peptides) thereof so long as the portion provides binding affinity and avidity to the subject IRAK3 polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like ATP or ATP analogs (for kinase assays), salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the IRAK3 polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the IRAK3 polypeptide and one or more binding targets is detected by any convenient way. For IRAK3 kinase assays, 'binding' is generally detected by a change in the phosphorylation of an IRAK3 substrate. In this embodiment, kinase activity may quantified by the transfer to the substrate of a labeled phosphate, where the label may provide for direct detection as radioactivity, luminescence, optical or electron density, etc. or indirect detection such as an epitope tag, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the IRAK3 polypeptide to the target in the absence of the agent as compared with the binding affinity in the presence of the agent indicates that the agent modulates the binding of the IRAK3 polypeptide to the IRAK3 binding target. Analogously, in the cell-based assay also described below, a difference in IRAK3-dependent transcriptional activation in the presence and absence of an agent indicates the agent modulates IRAK3 function. A difference, as used herein, is statistically significant and preferably represents at least a 50%, more preferably at least a 90% difference.

The following experimental section and examples are offered by way of illustration and not by way of limitation.

EXAMPLES

1. Protocol for at IRAK3 autophosphorylation assay.

A. Reagents:

Neutralite Avidin: 20 µg/ml in PBS.

kinase: $10^{-8}$–$10^{-5}$M IRAK3 kinase domain at 20 µg/ml in PBS.

substrate: $10^{-7}$–$10^{-4}$M biotinylated IRAK3 substrate at 40 µg/ml in PBS.

Blocking buffer: 5% BSA, 0.5% Tween 20 in PBS; 1 hour at room temperature.

Assay Buffer: 100 mM KCl, 10 mM MgCl$_2$, 1 mM MnCl$_2$, 20 mM HEPES pH 7.4, 0.25 mM EDTA, 1% glycerol, 0.5% NP-40, 50 mM BME, 1 mg/ml BSA, cocktail of protease inhibitors.

[$^{32}$P]γ-ATP 10×stock: 2×10$^{-5}$M cold ATP with 100 μCi [$^{32}$P]γ-ATP. Place in the 4° C. microfridge during screening.

Protease inhibitor cocktail (1000X): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM NaVo$_3$ (Sigma # S-6508) in 10 ml of PBS.

B. Preparation of assay plates:

Coat with 120 μl of stock N Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 40 μl biotinylated substrate (2–200 pmoles/40 μl in assay buffer)

Add 40 μl kinase (0.1–10 pmoles/40 μl in assay buffer)

Add 10 μl compound or extract.

Add 10 μl [$^{32}$P]γ-ATP 10×stock.

Shake at 25° C. for 15 minutes.

Incubate additional 45 minutes at 25° C.

Stop the reaction by washing 4 times with 200 μl PBS.

Add 150 μl scintillation cocktail.

Count in Topcount.

D. Controls for all assays (located on each plate):

a. Non-specific binding b. cold ATP at 80% inhibition.

2. Protocol for high throughput IRAK3-MyD88 binding assay.

A. Reagents:

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM MgCl$_2$, 1% glycerol, 0.5% NP-40, 50 mM β-mercaptoethanol, 1 mg/ml BSA, cocktail of protease inhibitors.

$^{33}$P IRAK3 polypeptide 10×stock: 10$^{-8}$–10$^{-6}$M "cold" IRAK3 supplemented with 200,000–250,000 cpm of labeled IRAK3 (Beckman counter). Place in the 4° C. microfridge during screening.

Protease inhibitor cocktail (1000X): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM NaVO$_3$ (Sigma # S-6508) in 10 ml of PBS.

TRAF2: 10$^{-7}$–10$^{-5}$M biotinylated MyD88 in PBS.

B. Preparation of assay plates:

Coat with 120 μl of stock N-Avidin per well overnight at 4° C.

Wash 2 times with 200μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-IRAK3 (20–25,000 cpm/0. 1–10 pmoles/well=10$^{-9}$–10$^{-7}$ M final conc).

Shake at 25° C. for 15 minutes.

Incubate additional 45 minutes at 25° C.

Add 40 μM biotinylated MyD88 (0.1–10 pmoles/40 ul in assay buffer)

Incubate 1 hour at room temperature.

Stop the reaction by washing 4 times with 200 μM PBS.

Add 150 μM scintillation cocktail.

Count in Topcount.

D. Controls for all assays (located on each plate):

a. Non-specific binding b. Soluble (non-biotinylated MyD88) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated polypeptide comprising a sequence of at least 25 consecutive amino acid residues of SEQ ID NO:2.

2. An isolated polypeptide according to claim 1, the sequence comprising at least 50 consecutive amino acid residues of SEQ ID NO:2.

3. An isolated polypeptide according to claim 1, the sequence comprising a subsequence selected from the group consisting of:

| | |
|---|---|
| SEQ ID NO:2, residues 1–10; | SEQ ID NO:2, residues 237–245; |
| SEQ ID NO:2, residues 12–21, | SEQ ID NO:2, residues 440–450; |
| SEQ ID NO:2, residues 25–37; | SEQ ID NO:2, residues 442–451; |
| SEQ ID NO:2, residues 42–59; | SEQ ID NO:2, residues 445–452; |
| SEQ ID NO:2, residues 62–71; | SEQ ID NO:2, residues 447–454; |
| SEQ ID NO:2, residues 72–85; | SEQ ID NO:2, residues 449–456; |
| SEQ ID NO:2, residues 88–89; | SEQ ID NO:2, residues 450–457; |
| SEQ ID NO:2, residues 105–112; | SEQ ID NO:2, residues 471–480; |
| SEQ ID NO:2, residues 116–122; | SEQ ID NO:2, residues 495–502; |
| SEQ ID NO:2, residues 120–128; | SEQ ID NO:2, residues 501–510; |
| SEQ ID NO:2, residues 175–182; | SEQ ID NO:2, residues 525–532; |
| SEQ ID NO:2, residues 180–195; | SEQ ID NO:2, residues 527–540; |
| SEQ ID NO:2, residues 201–208; | SEQ ID NO:2, residues 549–556; |
| SEQ ID NO:2, residues 213–222; | SEQ ID NO:2, residues 563–575; |
| SEQ ID NO:2, residues 222–230; | SEQ ID NO:2, residues 577–590; and |
| SEQ ID NO:2, residues 228–237; | SEQ ID NO:2, residues 589–596. |
| SEQ ID NO:2, residues 230–338; | |

4. An isolated polypeptide according to claim 1, the sequence comprising a subsequence of SEQ ID NO:2, residues 1–10.

5. An isolated polypeptide according to claim 1, the sequence comprising a subsequence of SEQ ID NO:2, residues 12–21.

6. An isolated polypeptide according to claim 1, the sequence comprising a subsequence of SEQ ID NO:2, residues 25–37.

7. An isolated polypeptide according to claim 1, the sequence comprising a subsequence of SEQ ID NO:2, residues 42–59.

8. An isolated polypeptide according to claim 1, the sequence comprising a subsequence of SEQ ID NO:2, residues 62–71.

9. An isolated polypeptide according to claim 1, the sequence comprising a subsequence of SEQ ID NO:2, residues 72–85.

10. An isolated polypeptide according to claim 1, the sequence comprising a subsequence of SEQ ID NO:2, residues 88–89.

11. An isolated polypeptide according to claim 1, the sequence comprising a subsequence of SEQ ID NO:2, residues 105–112.

12. An isolated polypeptide according to claim 1, the sequence comprising a subsequence of SEQ ID NO:2, residues 116–122.

13. An isolated polypeptide according to claim 1, the sequence comprising a subsequence of SEQ ID NO:2, residues 120–128.

14. An isolated polypeptide according to claim 1, the sequence comprising a subsequence of SEQ ID NO:2, residues 175–182.

15. An isolated polypeptide according to claim 1, the sequence comprising a subsequence of SEQ ID NO:2, residues 180–195.

16. An isolated polypeptide according to claim 1, the sequence comprising a subsequence of SEQ ID NO:2, residues 201–208.

17. An isolated polypeptide according to claim 1, the sequence comprising a subsequence of SEQ ID NO:2, residues 213–222.

18. An isolated polypeptide according to claim 1, the sequence comprising a subsequence of SEQ ID NO:2, residues 222–230.

19. An isolated polypeptide according to claim 1, the sequence comprising a subsequence of SEQ ID NO:2, residues 228–237.

20. An isolated polypeptide according to claim 1, the sequence comprising a subsequence of SEQ ID NO:2, residues 230–338.

21. An isolated polypeptide according to claim 1, the sequence comprising a subsequence of SEQ ID NO:2, residues 237–245.

22. An isolated polypeptide according to claim 1, the sequence comprising a subsequence of SEQ ID NO:2, residues 440–450.

23. An isolated polypeptide according to claim 1, the sequence comprising a subsequence of SEQ ID NO:2, residues 442–451.

24. An isolated polypeptide according to claim 1, the sequence comprising a subsequence of SEQ ID NO:2, residues 445–452.

25. An isolated polypeptide according to claim 1, the sequence comprising a subsequence of SEQ ID NO:2, residues 447–454.

26. An isolated polypeptide according to claim 1, sequence comprising a subsequence of SEQ ID NO:2, residues 449–456.

27. An isolated polypeptide according to claim 1, the sequence comprising a subsequence of SEQ ID NO:2, residues 450–457.

28. An isolated polypeptide according to claim 1, the sequence comprising a subsequence of SEQ ID NO:2, residues 471–480.

29. An isolated polypeptide according to claim 1, the sequence comprising a subsequence of SEQ ID NO:2, residues 495–502.

30. An isolated polypeptide according to claim 1, sequence comprising a subsequence of SEQ ID NO:2, residues 501–510.

31. An isolated polypeptide according to claim 1, the sequence comprising a subsequence of SEQ ID NO:2, residues 525–532.

32. An isolated polypeptide according to claim 1, the sequence comprising a subsequence of SEQ ID NO:2, residues 527–540.

33. An isolated polypeptide according to claim 1, the sequence comprising a subsequence of SEQ ID NO:2, residues 549–556.

34. An isolated polypeptide according to claim 1, the sequence comprising a subsequence of SEQ ID NO:2, residues 563–575.

35. An isolated polypeptide according to claim 1, the sequence comprising a subsequence of SEQ ID NO:2, residues 577–590.

36. An isolated polypeptide according to claim 1, the sequence comprising a subsequence of SEQ ID NO:2, residues 589–596.

37. An isolated polypeptide according to claim 1, the sequence comprising SEQ ID NO:2.

38. A method of screening for an agent which modulates a kinase activity, said method comprising the steps of:
   a. incubating a mixture comprising:
      i. an isolated kinase comprising the kinase domain of SEQ ID NO:2;
      ii. a substrate of said kinase; and
      iii. a candidate agent;
   under conditions whereby, but for the presence of said agent, said kinase phosphorylates said substrate at a reference kinase activity; and
   b. detecting phosphorylation of said substrate by said kinase to determine an agent biased kinase activity;
wherein a difference between the agent-biased kinase activity and the reference kinase activity indicates that said agent modulates the phosphorylation of said substrate by said kinase.

* * * * *